United States Patent [19]
Corrado

[11] Patent Number: 5,098,331
[45] Date of Patent: Mar. 24, 1992

[54] THERAPEUTIC CHEST DRESSING FOR BREASTS HAVING IMPLANTS

[75] Inventor: Mark W. Corrado, Mayfield Heights, Ohio

[73] Assignee: Leading Lady, Inc., Beachwood, Ohio

[21] Appl. No.: 562,241

[22] Filed: Aug. 3, 1990

[51] Int. Cl.$^5$ .............................. A41C 3/00; A41C 3/02
[52] U.S. Cl. .................................... 450/58; 450/1; 450/23; 450/76; 450/79; 450/80; 450/85; 2/73; 2/DIG. 6; 2/DIG. 7; 128/100.1; 128/101.1
[58] Field of Search ............. 2/73, 109, 163, 170, 2/DIG. 6; 128/157, 101.1, 100.1, 873, 845, 874, 846, 869; 450/1, 13, 18, 23, 40, 50, 57, 58, 59, 60, 70, 76, 79, 80, 82, 83, 85, 86, 87, 88

[56] References Cited

U.S. PATENT DOCUMENTS

| | | | |
|---|---|---|---|
| 1,062,858 | 5/1913 | Smith | 2/109 |
| 2,239,056 | 4/1941 | Schiffer | 450/59 X |
| 2,363,017 | 11/1944 | Plehn | 450/86 |
| 2,424,453 | 7/1947 | Glick | 2/42 |
| 2,454,152 | 11/1948 | Glick | 450/79 X |
| 2,579,546 | 12/1951 | Cadous | 450/83 X |
| 2,586,267 | 2/1952 | Schaumer | 450/70 |
| 2,662,522 | 12/1953 | Muller | 128/155 |
| 2,717,437 | 9/1955 | Mestral | 28/72 |
| 2,760,199 | 8/1956 | Champagne | 450/58 X |
| 2,782,418 | 2/1957 | Garson | 450/88 X |
| 3,040,750 | 6/1962 | Hurwitz | 450/88 X |
| 3,062,216 | 11/1962 | Stein | 128/467 |
| 3,256,886 | 6/1966 | Sachs | 450/59 |
| 3,298,366 | 1/1967 | Moore et al. | 128/157 |
| 3,411,510 | 11/1968 | Child | 450/70 |
| 3,548,833 | 12/1970 | Lavergne | 450/70 X |
| 3,561,442 | 2/1971 | Goswitz | 450/1 X |
| 3,665,929 | 5/1972 | Brantly | 450/70 |
| 3,698,399 | 10/1972 | Hand | 450/59 |
| 3,746,007 | 7/1973 | Hand et al. | 450/86 X |
| 3,779,250 | 12/1973 | Radomski | 450/70 X |
| 3,968,803 | 7/1976 | Hyman | 128/482 |
| 4,143,662 | 3/1979 | Fisher | 450/86 X |
| 4,767,377 | 8/1988 | Falla | 450/76 X |
| 4,957,466 | 9/1990 | Happs | 450/23 X |

FOREIGN PATENT DOCUMENTS

| | | | |
|---|---|---|---|
| 1086901 | 10/1980 | Canada | 450/1 |
| 0156518 | 10/1985 | European Pat. Off. | 450/1 |
| 75415 | 8/1949 | Norway | 450/60 |
| 365258 | 1/1932 | United Kingdom | 1/1 |
| 597485 | 2/1948 | United Kingdom . | |
| 714271 | 8/1954 | United Kingdom | 450/40 |

Primary Examiner—Werner H. Schroeder
Assistant Examiner—Jeanette E. Chapman
Attorney, Agent, or Firm—Body, Vickers & Daniels

[57] ABSTRACT

A therapeutic chest dressing for breasts having implants including a chest encircling, flexible band provided with front flaps whereby the band is disposed against the back of a person and the front flaps overlap and fasten to each other. A chest encircling strip is attached to the flexible band for preventing movement or distortion of the implants for breasts received in the flexible band.

14 Claims, 4 Drawing Sheets

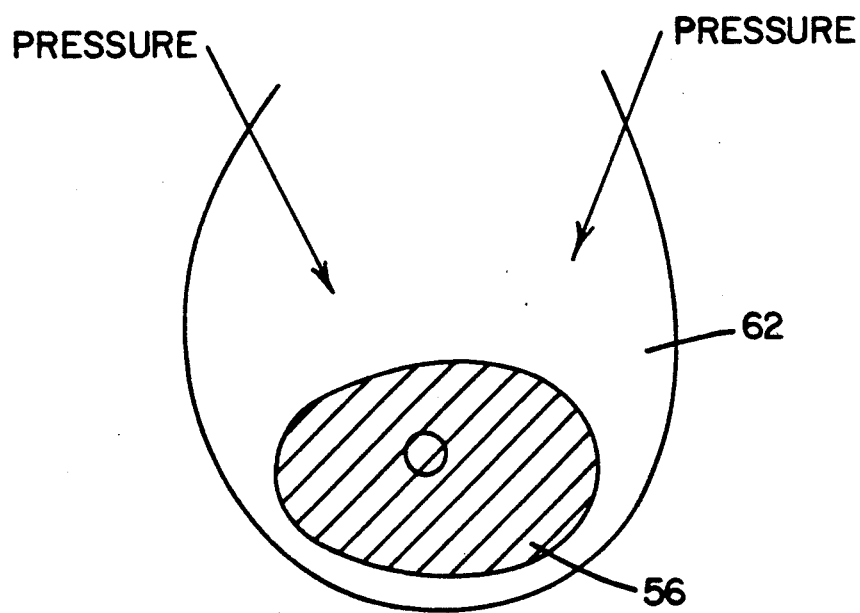

THERAPEUTIC CHEST DRESSING FOR BREASTS HAVING IMPLANTS

The present invention relates to the art of surgical chest dressings and more particularly to a therapeutic chest dressing having a support for preventing movement or distortion of implants in a breast.

The present invention is particularly applicable for use in a therapeutic chest dressing worn by a post-operative patient who has recently had implants inserted in one or more of her breasts and will be described with particular reference thereto; however, the invention has much broader applications and may be used in various other chest dressings or brassieres for persons requiring pressure to be exerted against the upper surface of their breasts to prevent movement thereof.

RELATED APPLICATIONS

This application relates to U.S. patent application Ser. No. 562,240, filed 8-3-90, entitled "Therapeutic Brassiere for Breasts Having Implants", filed concurrently herewith by a common assignee.

BACKGROUND OF THE INVENTION

After a surgical operation wherein an implant is inserted in one or both breasts of a person, there is a tendency for the implant to move or shift to an unwanted position or event distort its shape during the initial, post-operative healing process which typically lasts at least about one week. To overcome this tendency, it has been a common practice to first apply a chest dressing as disclosed in U.S. Pat. No. 3,968,803 and then further bind the breast with an elastic bandage, such as an ace bandage, which encircles the surgical dressing already applied to the patient for exerting pressure on the upper surface of the breast and pressing them towards the patient's chest. However, when the dressing had to be changed, the attachment of the elastic bandage was a difficult procedure which could not easily be done by the patient. Also, the force with which the bandage was applied to the breast had to be carefully controlled, which was somewhat difficult to manage due to the size of the body encircling bandage.

Moreover, in some instances, metal clips and fasteners were used to secure the elastic bandage about the chest dressing of the patient which clips and fasteners when contacting the skin could cause ancillary irritation.

THE INVENTION

The present invention relates to a chest encircling device structure which for use by a patient to prevent movement or distortion of an implant in one or more breasts. In accordance with the present invention, there is provided an improved therapeutic chest dressing comprising a chest encircling, flexible band formed primarily from a stretchable material. This band has a longitudinally continuous back portion adapted to lie against the back of a person using the dressing. The continuous back portion has two longitudinally spaced ends with each of the ends connected to one of a pair of front flaps. These front flaps include free ends spaced from the back portion and overlapping each other at engaging surfaces when the dressing is wrapped around a patient using the same. A two element, contact sensitive, reusable fastening means for releasably securing the free ends together in selected, adjustable longitudinal positions is provided for closing the bandage around the patient. One element of the fastening means is secured onto each of the engaging surfaces of the free ends of the front flaps.

In accordance with the preferred embodiment of the present invention, the contact sensitive, reusable fastening means are "Velcro" fasteners which are disclosed in U.S. Pat. No. 2,717,437. This patent is incorporated by reference herein and includes a disclosure of a fastening means including a gripping strip having a number of small, outwardly extending, closely spaced flexible hooks which hooks engage the strands of a loosely knitted, velvet type fabric by a transverse engagement of the strip having the hooks with the velvet-like fabric. This type of fastening means is well known and involves no metal elements. In addition, the fastening means is infinitely variable in that the gripping strip because the hooks can be positioned at various locations on the fabric strip to adjust the position of the two flaps of the strips with respect to each other.

A chest encircling strip is attached to the chest encircling band for preventing movement or distortion of the implant in each breast received within the chest encircling band. The chest encircling strip exerts pressure on the upper surface of the dressing encased breasts by pressing them towards the chest of the patient using the therapeutic chest dressing. The chest encircling strip is an elastic material attached to the back portion of the chest encircling band which is adapted to be positioned at approximately the center of the wearer's back. The chest encircling strip has free ends and means for fastening the free ends to the strip to form an unending loop. The fastenening structure includes first and second reusable fastening elements secured to one side of the strip so that a first element is located at a first free end of the band and a second element is in spaced relationship to the first element. Third and fourth reusable fastening elements are secured to a second side of the strip. The third fastening element is located at a second free end of the strip and the fourth fastening element is displaced in spaced relationship to the third fastening element. When securing the strip to the patient, the first fastening element is initially fastened to the fourth fastening element and then the second fastening element is fastened to the third fastening element.

By adopting an improved therapeutic chest dressing of the type described above, the back portion of the dressing may be slipped under the patient without disrupting anesthetic apparatus or any intravenous needles. After a dressing is placed over the closed incision, the dressing is closed in the front and drawn snug by a proper closing of the front flaps with the variable fastening means. Thereafter, the chest encircling strip is bound about the dressing encased patient's breasts and adjusted to exert the proper pressure by fastening the free ends. More specifically, a section of the strip is pressed against the dressing encased breasts to exert the proper pressure. Then, a second section of the strip is wrapped around the chest and the fourth fastening element which is spaced from the free end of the second section of the band is secured against the first fastening element on the free end of the first section of the strip. Then to insure that the band is secure, the third fastening element on the free end of the second section of the band is secured against the second fastening element which is in spaced relationship to the first fastening element on the first portion of the band. In this manner no metallic clips are required, an infinitely variable bandage is provided, and the patient need not be disturbed while the dressing is being applied. The dressing is variable in size because of the fastening means used.

In addition, the flexible band extending around the chest of the patient is formed from a stretchable material which stretches in all directions to conform with both the natural shape of the breast and the dressing on the patient's closed incision. The term "stretchable" is distinguished from elastic in that a stretchable material conforms to the body shape without exerting substantial pressure. An elastic material has a higher and more pronounced return capability so that when elongated, a returning force is exerted which returning force is quite high and proportional to the amount of elongation. In the fabric art, the difference between stretchable and elastic fabrics are well known. The elastic fabrics tend to bind and exert confining pressure.

In accordance with another aspect of the invention, the front flaps are provided with two stretchable portions sewed together to provide an outwardly protruding profile which will accommodate the dressing and the natural shape of the breast when the bandage is used for a chest implant patient.

In accordance with another aspect of the invention, the chest encircling strip is formed of an elastic material which tends to bind and exert confining pressure on the breast. In addition, the elastic band is variable in size because of the fastening means used.

The primary object of the present invention is the provision of a therapeutic chest dressing for preventing movement or distortion of breast implants. In addition, the dressing allows easy changing of the absorbent dressing on the closed incision by merely opening the front of the dressing and replacing the absorbent dressing over the incision. This can be done without lifting the patient and quite rapidly by a nurse or other attendant. The improved therapeutic dressing or bandage explained above also provides sufficient support for the unoperated breast and does not distort the breast during post-operative convalescence by the patient.

Another object of the present invention is the provision of a therapeutic chest dressing which provides proper support for the absorbent dressing and still is acceptable and comfortable to the patient.

Yet another object of the present invention is the provision of a therapeutic chest dressing that can be applied to a patient of either sex in the operating room while the patient is still under the influence of an anesthesia without disturbance of the anesthetic equipment, the position of the arms of the patient or any other equipment connected to the patient during the operating procedure.

Another object of the present invention is the provision of a therapeutic chest dressing that can be conveniently placed under the back of a patient while on the operating table and closed from the front without using metallic clips or elastic bandaging.

Another object of the present invention is the provision of an improved therapeutic chest dressing as defined above which does not restrict the patient's respiration or cause skin irritation due to the existence of metal clips or clamps.

Yet another object of the present invention is the provision of a therapeutic chest dressing as defined above, which dressing allows for the changing of the dressing with a minimum inconvenience of the patient.

Yet another object of the present invention is the provision of a therapeutic chest dressing as defined above, which dressing is inexpensive to produce and can be applied to the patient with a minimum of patient disturbance and a minimum of time.

These and other objects and advantages will become apparent from the following description taken together with the accompanying drawings in which.

PREFERRED EMBODIMENT

Figure 1:
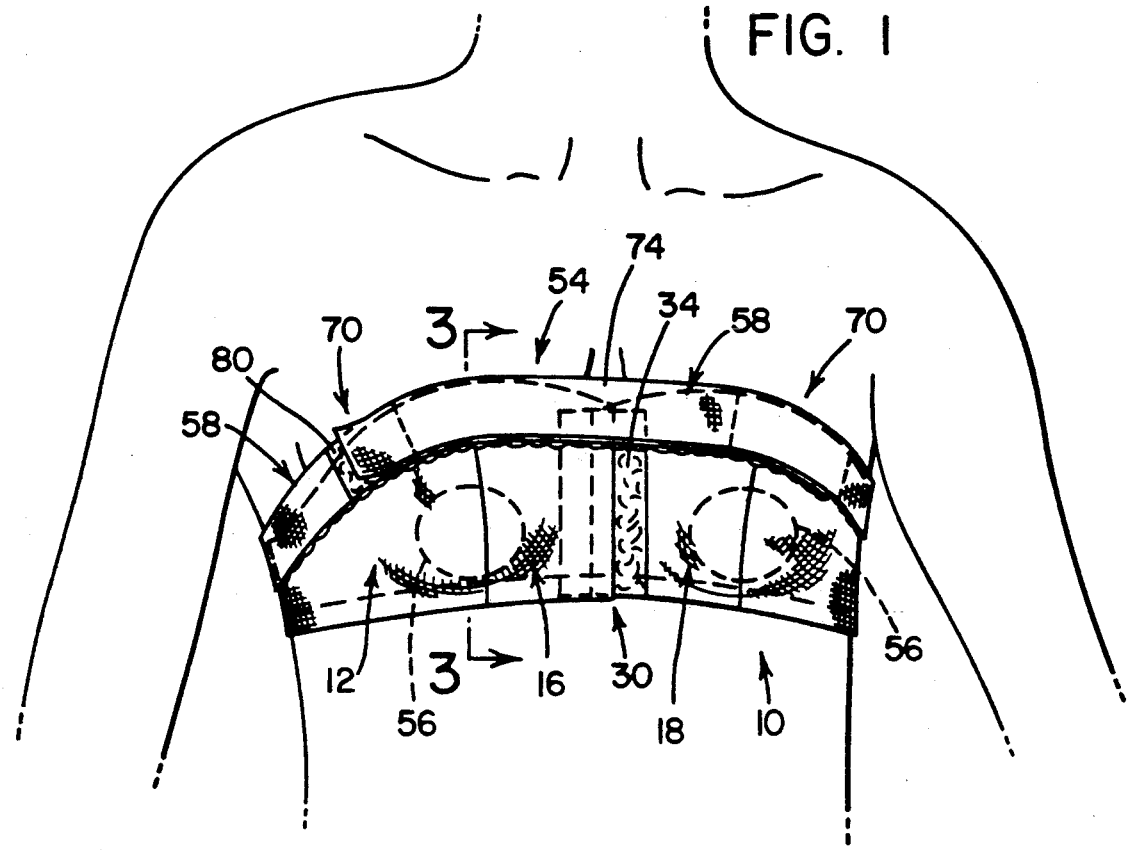
FIG. 1 is a front view showing a patient with a breast implant having a therapeutic chest dressing in the closed condition in a accordance with the preferred embodiment of the present invention.
Figure 2:
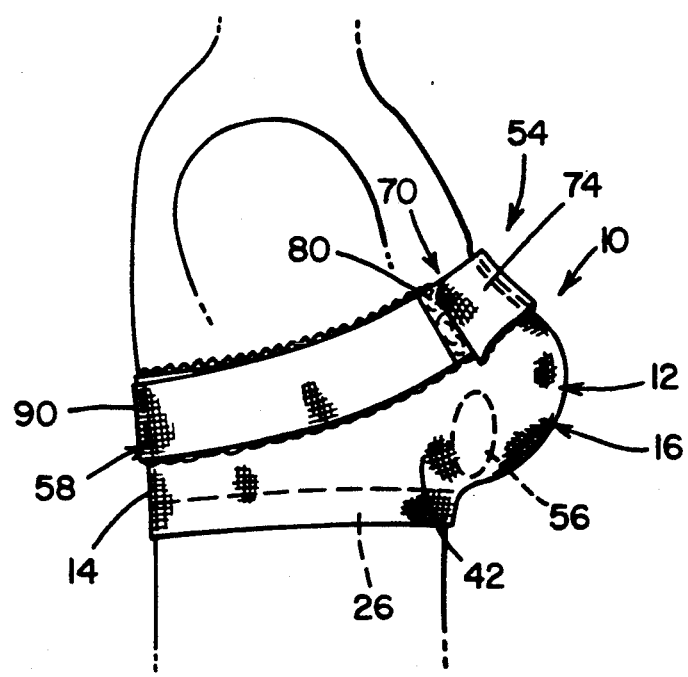
FIG. 2 is a side view of a patient with a breast implant wearing a therapeutic chest dressing constructed in accordance with the preferred embodiment of the present invention.
Figure 4:
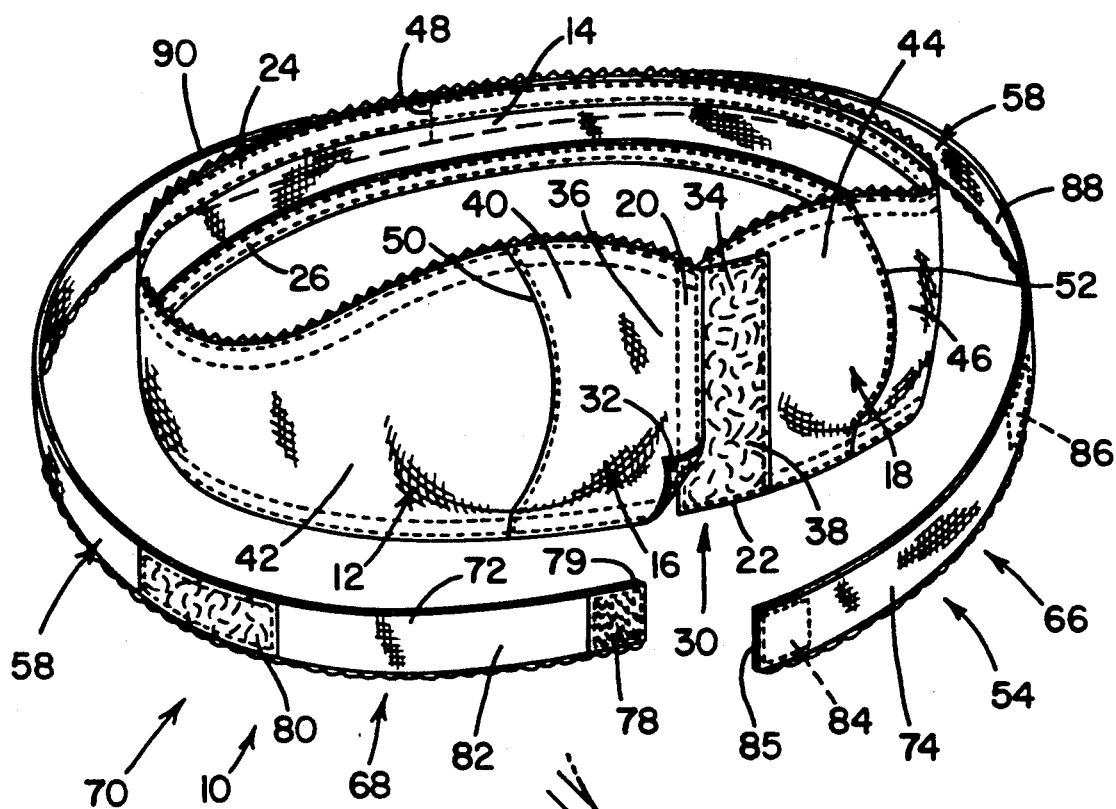
FIG. 4 is a perspective view of a therapeutic chest dressing in accordance with the present invention.
Figure 5:
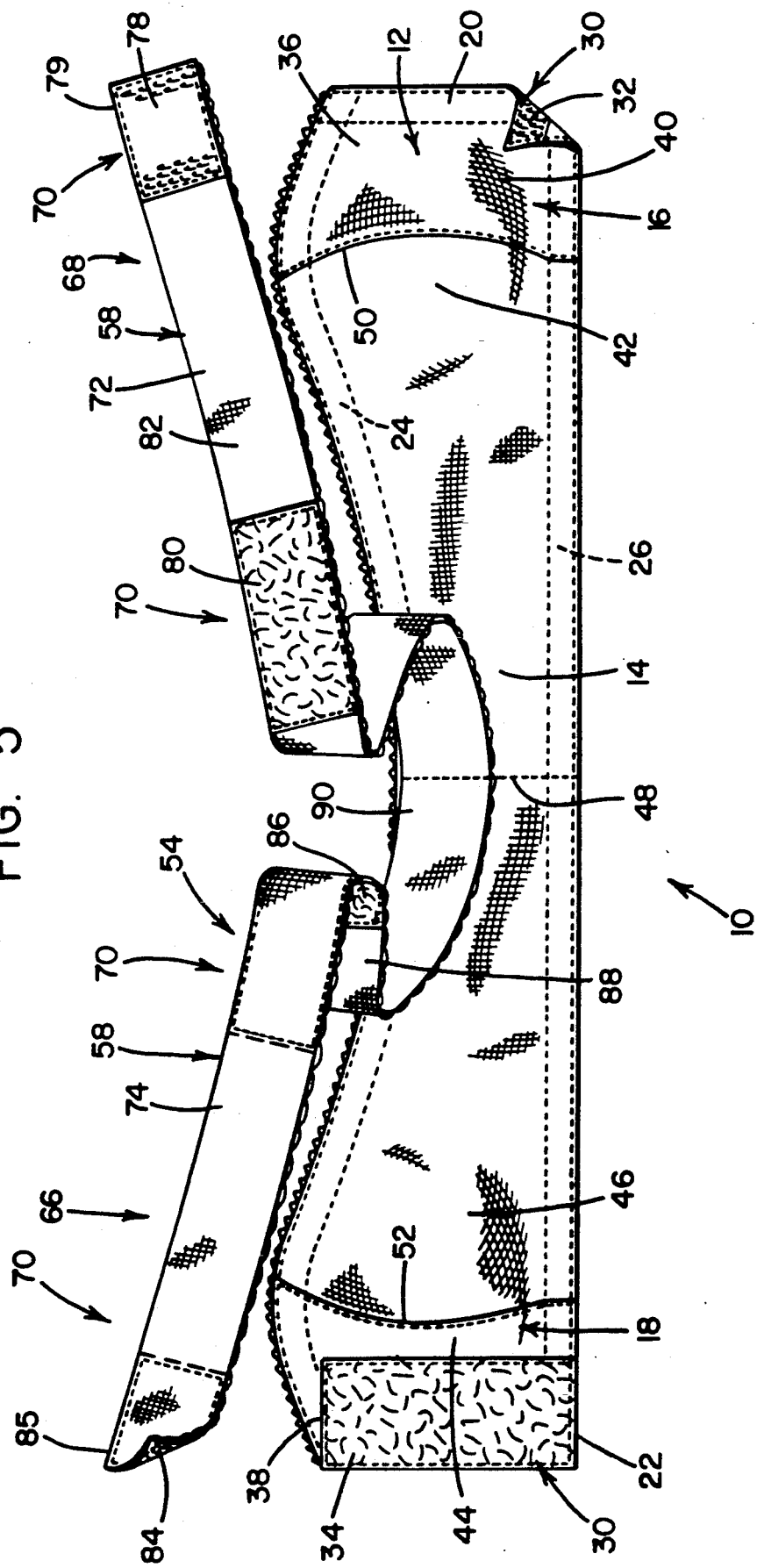
FIG. 5 is a rear view of a therapeutic chest dressing in accordance with the present invention; and, FIG. 6 is a view illustrating the force of the therapeutic chest dressing on a breast having an implant.

Referring now to the drawings wherein the showings are for the purpose of illustrating the preferred embodiment of the invention only, and not for the purpose of limiting same, FIGS. 4 and 5 show a therapeutic surgical chest dressing 10 for the breasts having implants of an operative patient as shown in FIGS. 1 and 2.

In accordance with the preferred embodiment of the invention, chest dressing 10 which may be referred to as a bandage, includes a flexible band 12 formed primarily from a stretchable, but non-elastic fabric or material. This definition is well known in the art and in practice is a loose weave, porous 100% knit Nylon which allows freedom of movement of the material in all directions and a low recovery force so that the material does not exert substantial pressure on the patient during use of the dressing or bandage. Flexible band 12 includes a back engaging portion 14 which is longitudinal and continuous without fasteners or other coupling devices. Although band 12 is preferably stretchable material throughout its length, it is possible to provide certain areas with other materials without departing from the intent of the invention. The extended ends of back portion 14 merge into two joined front flaps 16 and 18 having free ends 20, 22 which overlap when the dressing or bandage is in place around a surgical patient. An undulating upper marginal strip 24 is provided around the upper portion of flexible band 12. In a like manner, a generally straight lower marginal strip 26 is provided along the lower portion of flexible band 12. These two marginal strips are formed from elastic material which provides the strength for the bandage or dressing in the longitudinal direction so that the bandage holds the general position shown in FIGS. 1 and 2. The free ends 20, 22 overlap in the front when the bandage or dressing 10 is in place around a post-operative patient.

The overlapping surfaces of these free ends 20, 22 are provided with a two element, contact sensitive, reusable fastening means 30 to provide infinitely selected longitudinal positions within a given general range determined by the elements forming the fastening means. Means 30 include no metal elements and are in the preferred embodiment, a Velcro fastener wherein the first element 32 is a transversely extending gripping strip including a number of small, outwardly extending, closely spaced flexible hooks which take on the appearance of a rough fabric. The second element 34 is a fabric strip extending transversely of flexible band 12 and interlocks with the hooks of gripping strip 32. This second element assumes the normal appearance of a velvet fabric. Strips 32, 34 are non-elastic and non-stretchable to provide transverse stability for bandage or dressing 10. These strips extend between the elastic strips 24, 26 to complete the boundary for the bandage and provide the final dimensional stability and general strength for the bandage. The overlapping surfaces onto which elements 32, 34 are provided are designated 36, 38 respectively, in FIGS. 4 and 5. These overlapping surfaces are at the free ends 20, 22 of front flaps 16, 18.

Referring now more particularly to the front flaps 16, 18, these flaps are formed by two separate pieces of stretchable material. Front flap 16 includes pieces 40, 42, while front flap 18 includes pieces 44, 46. Thus, the internal structure of flexible band 12 includes four separate stretchable, non-elastic panels. The panels 42, 46 are jointed at the back portion 14 by a transverse seam 48 which is loosely sewn to allow normal transverse stretching of the pieces or panels 40, 44. It is, of course, within the terms of the present invention for panels 40, 42 to be constructed as a continuous, longitudinally extending panel.

Pieces or panels 40, 42 are joined together by a seam 50. In a like manner, panels 44, 46 are joined together by a seam 52. Seams 50, 52 are longer than the non-stretched, transverse dimension so that forwardly extending profiles are created at the forward portions of front flaps 14, 16. This forward contour allows better conformity to both the breast having an implant and to the non-operated breast of a post operative patient. It is also within the terms of the present invention for the seams 52, 54 to be eliminated and a single panels used in forming the front flaps 16, 18.

As so far described, flexible band 12 can be wrapped around a post surgical patient and connected at the front by strips 32, 34. Strips are secured together by engaging strip 32 at a selected position on strip 32.

A further aspect of the present invention relates to a means 54 attached to the chest encircling band 12 for preventing movement or distortion of the implant 56 in each breast received in one or more of the breast receiving sections or flaps 16 and 18. The means 54 for preventing movement or distortion comprises a body encircling strip 58 for exerting pressure on the upper surface 60 of the breasts 62 by pressing them toward the chest 50 of the patient wearing the therapeutic chest dressing.

Referring to FIGS. 4 and 5, the body encircling strip 58 comprises a strip of elastic material attached to the back engaging surface 14 of the chest encircling band 12. The attachment of the strip 58 is preferably at a location near the center of the wearer's back and most preferably the connection is along the transverse seam 48.

Figure 3:
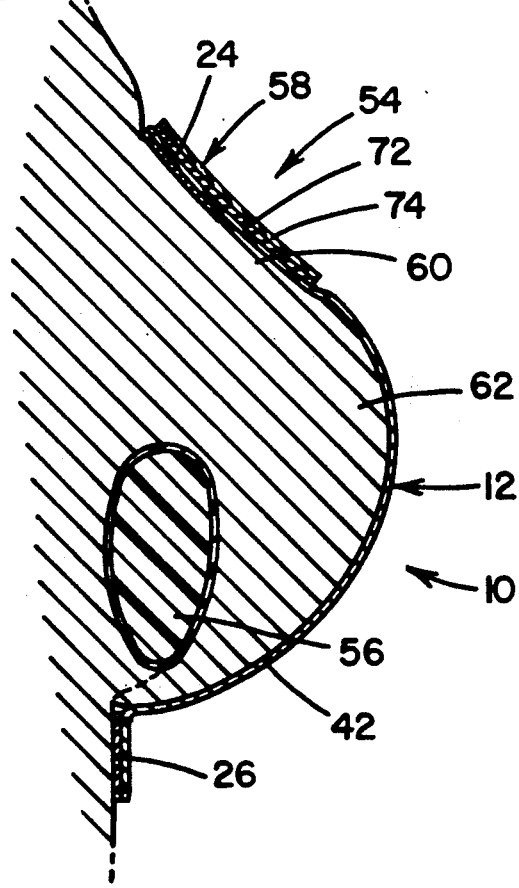
FIG. 3 is a view illustrating the therapeutic chest dressing of the present invention on a breast having an implant.

The body encircling strip 58 of chest dressing 10 has extended free ends 66 and 68 which overlay in the front when the chest encircling band and the body encircling strip are in place as illustrated in FIGS. 1 and 2. Further, the strip 58 includes means 70 for fastening free ends 66 and 68 to form the strip into an unending loop encircling the patient's chest. As seen in FIGS. 1, 2 and 3, the body encircling strip 58 presses against the breast receiving sections of the chest encircling band 12 to exert pressure on the breasts of the patient when the free ends 66 and 68 are wrapped around the chest encircling band 12.

The body encircling strip 58 includes overlapping surface sections 72 and 74 of the free ends 66 and 68. The overlapping surface sections 72 and 74 are each provided with contact sensitive, reusable fastening means 70 at the ends of each of the sections for releasably fastening the free ends 66 and 68 of the band together in selected, longitudinal positions. It is understood that the infinitely selected longitudinal positions extend within a given general range determined by the elements forming the fastening means. The fastening means 70 includes first and second reusable fastening elements 78 and 80 secured to a first side 82 of the strip 58. The first fastening element 78 is located at one end 79 and the second element 80 is disposed in spaced relationship to the first element 78. Moreover, third and fourth reusable fastening elements 84 and 86 are secured to a second side 88 of the strip. The third fastening element 84 is located at the other end 85 of the strip 58 and the fourth fastening element 86 is in spaced relationship to the third fastening element.

The body engaging strip 58 includes a flexible strip formed primarily of an elastic fabric or material. The strip includes a back engaging portion 90 which overlies the back engaging portion 14 of the flexible band 12. The back engaging portion 90 is longitudinal and continuous without fasteners or other coupling devices. Although the strip is preferably an elastic material throughout its length, it is possible to provide certain areas with other material without departing from the intent of the invention. The extended free ends 66 and 68 of the back portion 90 merge into two joined overlapping front sections 72 and 74 which overlap when the strip is placed around a patient subsequent to the dressing being in place around a post-operative patient. The strip 58 is attached along the back engaging section 90 to the flexible band 12. Preferably, the attachment is along the transverse seam 48. The attachment of the strip to the band 12 forming a combined therapeutic dressing structure 10 is an important aspect of the invention because it stabilizes the location of the strip 58 with respect to the dressing band 12 and thereby insures that the appropriate pressure is applied to the upper surface of the breast so that the implant is held in place. Note that the strip 58 is attached to the upper portion of the flexible band 12 and preferably overlies the upper marginal strip 24. This position reduces the tendency of the strip 58 to cause the lower marginal strip 26 from riding up on the patient's back.

The fastening means 70 on overlapping surface sections 72 and 74 of the free ends 66 and 68 are provided with two element, contact sensitive, reusable fastening means to provide infinitely selected longitudinal positions within a given general range determined by the elements forming the fastening means 70. These strips are substantially unstretchable and therefore give the overlapping sections a substantially non-stretched, transverse dimension. Fastening means 70 preferably include no metal elements and are in the preferred embodiment, a Velcro fastener wherein the first and third fastening elements 78 and 84 comprise transversely extending gripping strips including a number of small, outwardly extending, closely spaced flexible hooks which take on the appearance of a rough fabric. The second and fourth fastening elements 80 and 86 comprise a fabric strip, extending transversely of flexible strip 58, which interlocks with the hooks of gripping strips 78 and 84, respectively. The second and fourth fastening elements 80 and 86 assume the normal appearance of a velvet strip. The provision of the fastening elements 78, 80, 84 and 86 provide transverse dimensional stability and general strength to the strip 58.

After the flexible band 12 is wrapped around a surgical patient and connected at the front fastening strips 30 and 34, the extended free ends of 66 and 68 of back portion 90 are wrapped around the chest of the post-surgical patient so that the section 74 overlaps the section 72. Then, first fastening element 78 is secured to the fourth fastening element 86 to provide the appropriate pressure against the upper surface of the breast 62. Then, to insure that the strip 58 does not unwrap, the third fastening element 84 is fastened to the second fastening element 80 so that the body encircling strip 58 is positioned as shown in FIGS. 1 and 2. To change the dressing 10, it is only necessary to first unfasten the unwrap the strip 58 and then to open the front of the band 12. This may be done quite easily by a relatively untrained person or by the patient himself.

Although the fastening means for the flexible band 12 and the body engaging strip 58 are disclosed as including no metal elements, it is within the scope of the present invention to substitute any fastening means including those with metal elements as required.

The patents disclosed herein are incorporated in their entirety by reference herein.

The invention has been described with reference to a preferred embodiment and it is apparent that many modifications may be incorporated into the design and configuration of the therapeutic chest dressing for breasts having implants discussed herein without departing from the spirit or the essence of the invention. It is my intention to include all such modifications and alterations insofar as they come within the scope of my invention. It is thus the essence of my invention to provide a therapeutic chest dressing which can be readily adapted and configured to be incorporated in a wide variety of applications.

Wherefore, it is claimed:

1. A therapeutic chest dressing for breasts having implants, comprising:
   a chest encircling stretchable band of material having two breast receiving sections, said band of material having free ends and means for fastening the free ends of the band together to affix the chest dressing to the body of the person using said dressing; and,
   means attached to the chest encircling band for pressing the breasts of the person using said dressing disposed within chest band against the body of the person to prevent movement or distortion of the implant in the breasts received in the breast receiving sections.

2. The therapeutic chest dressing of claim 1 wherein said means for pressing comprises a body encircling strip means for pressing against the breasts of the person using the dressing by wrapping the strip means around the stretchable band affixing the therapeutic chest dressing to the person.

3. The therapeutic chest dressing of claim 2 wherein said body encircling strip means comprises a strip of elastic material attached to a back portion of the chest encircling band adapted to be generally positioned at the center of the person's back.

4. The therapeutic chest dressing of claim 3 wherein said body encircling strip means is disposed against the breast receiving sections of the chest encircling band for pressing the breasts of the person using the dressing against their body.

5. The therapeutic chest dressing of claim 4 wherein said body encircling strip has free ends partially overlapping each other and means for fastening the free ends of said strip to form the strip into an unending loop encircling the chest of the person using said dressing.

6. The therapeutic chest dressing a claim 5 wherein the means for fastening the free ends to the strip, comprises:
   first and second reusable fastening elements secured to a first side of said strip, said first fastening element being located at one end of said strip and said second fastening element being in spaced relationship to said first fastening element;
   third and fourth reusable fastening elements secured to a second side of said strip, said third element being located at the other end of said strip and said fourth fastening element being in spaced relationship to said third element; and,
   whereby said first element is fastened to said fourth element and said second element is fastened to said third element.

7. The therapeutic chest dressing of claim 6 wherein said first and third fastening elements and said second and fourth fastening element are joinable in variable positions.

8. The therapeutic chest dressing of claim 7 wherein the fastening elements comprise contact sensitive, reusable fastening members for releasably fastening said elements together in selected, adjustable longitudinal positions.

9. The therapeutic chest dressing of claim 8 wherein said first and third elements of said contact sensitive, reusable fastening members are gripping strips including a number of small, outwardly extending, closely spaced flexible hooks and said second and fourth elements are fabric strips into which said hooks are releasably engaged by contact of said gripping strips with said fabric strips.

10. The therapeutic chest dressing of claim 5 wherein the fastening means comprises contact sensitive, reusable fastening members for releasably fastening the free ends of said band together in selected, adjustable longitudinal positions.

11. The therapeutic chest dressing of claim 10 wherein
   said chest encircling band has a longitudinally continuous back portion adapted to lie against the back of a person using said chest dressing;
   said continuous back portion has two longitudinally spaced ends, with each of said ends connected to one of a pair of front flaps; and
   said front flaps including free ends spaced from said back portion and overlapping each other at engaging surfaces when said dressing is wrapped around a person using the same.

12. The therapeutic chest dressing of claim 11 wherein each of said front flaps has a non-stretched transverse dimension at a position and include two stretchable material panels jointed together at said position with a seam which is substantially greater than said transverse dimension whereby said front flaps can assume a non-stretched outwardly protruding profile.

13. The therapeutic chest dressing of claim 12 wherein said stretchable material is stretched in all directions.

14. The therapeutic chest dressing of claim 13 wherein said flexible band includes upper and lower longitudinally extending elastic marginal body engaging bands to define outer engaging surfaces for said chest dressing.

* * * * *